United States Patent [19]

Hill et al.

[11] 4,164,943

[45] Aug. 21, 1979

[54] CATHETER ANCHOR

[75] Inventors: J. Donald Hill, San Francisco; Gordon H. Fountain, Oakland, both of Calif.

[73] Assignee: Thoratec Laboratories Corporation, Emeryville, Calif.

[21] Appl. No.: 838,320

[22] Filed: Sep. 30, 1977

[51] Int. Cl.[2] .......................................... A61M 25/02
[52] U.S. Cl. .................................. 128/348; 128/133; 128/DIG. 26
[58] Field of Search ........... 128/133, 214 R, 348–351, 128/DIG. 26

[56] References Cited

U.S. PATENT DOCUMENTS

| | | | |
|---|---|---|---|
| 2,046,094 | 6/1936 | Schmidt | 128/349 R |
| 2,670,735 | 3/1954 | Brody | 128/133 |
| 3,371,352 | 3/1968 | Siposs et al. | 3/1.5 |
| 3,630,195 | 12/1971 | Santomieri | 128/133 |
| 3,696,920 | 10/1972 | Lahay | 206/63.2 R |

FOREIGN PATENT DOCUMENTS 624676  8/1961  Canada ............................ 128/DIG. 26

*Primary Examiner*—Dalton L. Truluck
*Attorney, Agent, or Firm*—Lothrop & West

[57] ABSTRACT

A catheter anchor for holding a catheter in position in a patient has a base in the form of a disc with a flat surface normal to a central axis. There is a transverse, resilient bar extending across the disc on the side opposite the flat surface. The bar has at least one reentrant groove in it to receive and grasp the catheter. There may be an additional reentrant groove in the bar expandable by a plug to constrict the catheter groove. Also, there may be a pawl sheet adapted to grip the catheter and abut the bar to inhibit unwanted insertion of the catheter into the patient. From the flat surface of the disc a number of needles extend approximately helically and symmetrically with the axis and with their exposed points engageable with the patient's tissue by rotation. There may also be a central guide needle extending from the flat surface along the axis.

7 Claims, 4 Drawing Figures

CATHETER ANCHOR

BRIEF SUMMARY OF THE INVENTION

It is quite customary to utilize catheters, usually relatively small, resilient and flexible tubes, to extend from outside a patient's body into and through his tissue for the introduction of liquid into his veins and for many other purposes. There is a problem in making sure that the catheter remains in desired position despite movement of the patient and various other disturbing factors. It is important that a catheter, once inserted, not be inserted any farther because of the chance of introducing contamination into the wound, although it is permissible for the catheter in many instances to be partially or entirely withdrawn without harm. In practice, the surgeon not only introduces a catheter into position but fixes the catheter in position by affording a number of special stitches through the patient's tissue and around the catheter to make certain that there is no dislodgment. Since this requires additional effort and time, it is sometimes not practiced. There is a tendency for unsecured catheters to become dislodged or partially withdrawn or even to be accidentally inserted farther than intended. The present arrangement is of a structure that can be easily sterilized, can readily be engaged with the tissue of a patient and can hold a catheter without dislodgment despite many disturbing influences. The device permits withdrawal of the catheter readily and detachment of the device but does not permit further entry of the catheter.

DETAILED DESCRIPTION

Figure 1:
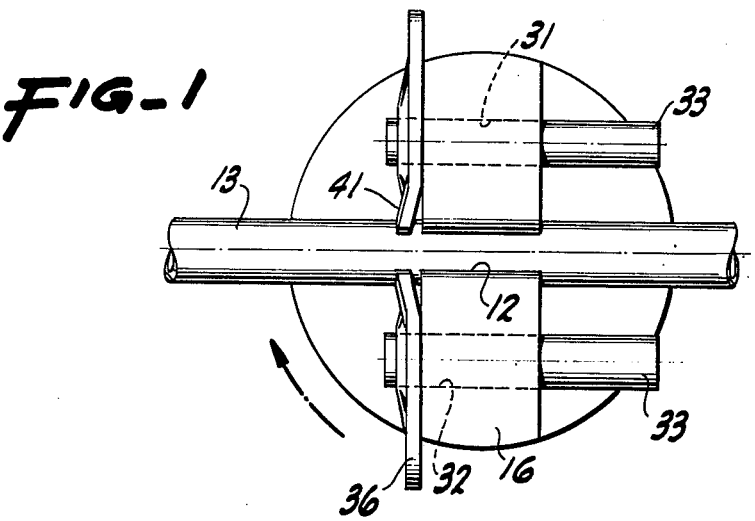
FIG. 1 is a plan of an unattached catheter anchor constructed pursuant to the invention and showing a catheter in position therewith.

Pursuant to the invention, there is provided a catheter anchor including a preferably unitary base 6 fabricated of somewhat resilient material inexpensive enough to be disposed of after a use or of material readily sterilized for reuse. The base is conveniently inclusive of a circular-cylindrical disc 7 having a flat lower surface 8 normal to a central axis 9. Upstanding from the disc and included in the base 6 is a bar 11 extending transversely of the disc and projecting far enough to serve as a grasping member. The bar has in its upper portion a transversely extending, reentrant groove 12, the groove having a circular portion that is approximately the size of a catheter 13 to be anchored. The circular portion rather smoothly opens outwardly and has curved walls 14 converging with the arcuate outer surface 16 of the bar. Since the material of the bar and preferably of the entire base is slightly resilient or deformable, the dimensions of the groove 12 need not be maintained exactly but are sized so the groove walls will frictionally engage the catheter 13 to be utilized therewith.

Preferably embedded in the disc 7 is a plate 17, conveniently of metal, to which is secured a metal ring 18, such as a wire ring, from which extend at approximately equal intervals a plurality of peripheral needles 19, 20 and 21. Any convenient number of needles can be used, but three are appropriate. The needles extend from the ring 18 first in a direction approximately parallel to the axis 9. They then curve to conform to a shape having a substantially helical portion 22 and ending in a sharp point 23 lying almost parallel to the surface 8 but having an axial component continuing the helical configuration. While the needles 19, 20 and 21 can be individually different under certain circumstances, it is customary to make them all substantially identical. There is also, in most cases, a central needle 26 extending from the plate 17 along the axis 9 and having its point 27 extending in the same direction and in advance of the points of the needles 19, 20 and 21.

Figure 3:
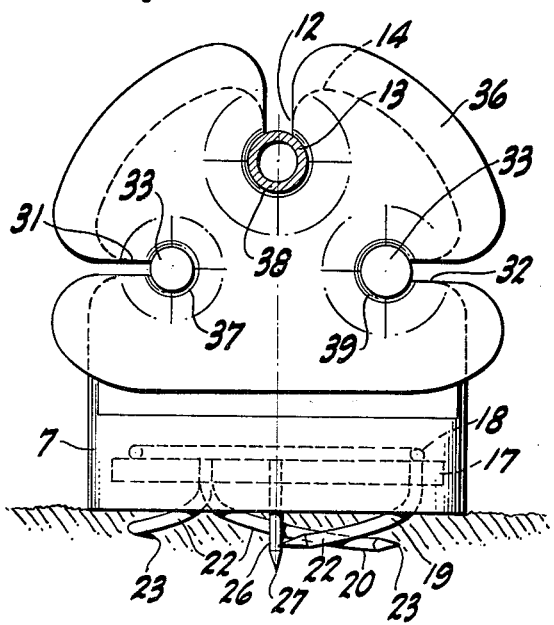
FIG. 3 is an end elevation of the structure shown in FIG. 1 and the patient's tissue being shown as in FIG. 2.
Figure 2:
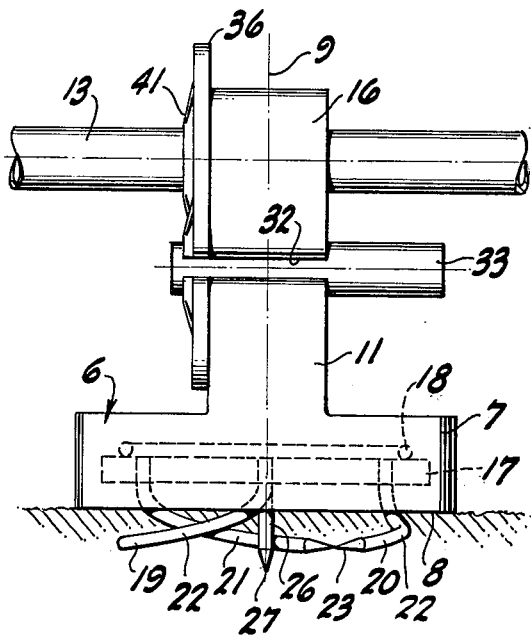
FIG. 2 is a side elevation of the device of FIG. 1, a portion of the patient's tissue with which the device is used being disclosed in cross-section.
Figure 4:
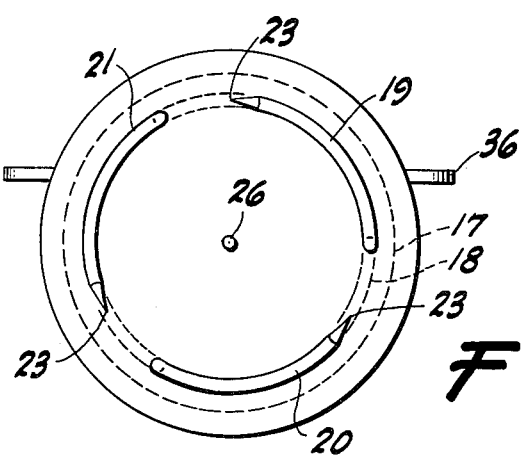
FIG. 4 is a view from below of an unattached catheter anchor.

In the use of the device, the surgeon grasps the bar 11 and brings the disc into close proximity with the flesh of the patient in the general zone in which the catheter 13 is to be employed. The surgeon brings the needles into contact with the tissue, the needle 26 first piercing and serving as a central locator and guide. He then rotates the bar 11 and the disc 7 in a generally clockwise direction (as the needles are disposed in this instance), and with a twisting and downward motion introduces the needles into the patient's tissue and rotates the base 6 through approximately a quarter turn so that the needles are all firmly embedded, as shown in FIGS. 2 and 3. By orienting the bar 11 correctly just before beginning the rotation of the base, the device can be finally positioned and the needles embedded with the bar extending approximately transversely of the desired direction of extension of the catheter 13.

There is thus provided a firmly established base united temporarily with the patient's tissue. The surgeon then introduces a catheter, such as 13, into the reentrant groove 12, forcing or snapping the catheter into position. There may be a slight looseness afforded at this stage. It is helpful to provide additional reentrant grooves 31 and 32 in the bar 11. Plugs 33 can be introduced into one or both of the additional reentrant grooves 31 and 32. The plugs are effective to deform the material of the bar in a manner to constrict the groove 12 so as more tightly to grip the catheter therein. The additional reentrant grooves 31 and 32 may also be employed for anchoring additional catheters of the same or different diameter.

Under many circumstances this is an adequate anchor for the catheter, but under extreme conditions a further holding device may be employed. Such a device can be a pawl sheet 36, a sheet of relatively resilient material, slightly larger in extent than the bar 11 and itself having a number of reentrant, matching openings 37, 38 and 39 therein. The openings 37, 38 and 39 are somewhat smaller than the catheter 13 and the plugs 33. When the sheet 36 is engaged with the catheter and the plugs, the sheet material tends to be displaced slightly away from the bar. This affords deformed portions 41 engaging the catheter, for example, at a slight, jamming angle. If the catheter 13 tends to move toward the right in FIG. 1, the jamming portions or deformed portions 41 then act as pawls and hold the catheter frictionally against any further entering movement into the wound. At the same time, when the catheter is moved toward the left in FIG. 1 from the base, the deformed portions 41 of the pawl sheet swing away and permit the catheter to be moved in that direction.

With this means, the surgeon can readily provide a stable anchor for the catheter in virtually any location and can be assured that a properly positioned catheter will remain in place despite extraneous disturbing forces. When the device is no longer needed, the catheter and base can be moved by first taking the catheter out of the reentrant portion and then rotating the base in the opposite direction. The remaining puncture wounds can readily be taken care of, and the device can either be discarded or sterilized for subsequent utilization.

We claim:

1. A catheter anchor comprising a base having a portion adapted to extend substantially parallel to subjacent skin, means including a plurality of needles fixed on said base and extending from said parallel portion in paths similarly helical with respect to said parallel portion for substantially simultaneously piercing and interengaging with said skin upon rotation of said base relative to said skin, and means on said base for holding a catheter.

2. A device as in claim 1 in which each of said needles has an approximately helical portion ending in a point.

3. A device as in claim 1 in which said base is a disc with a substantially flat surface, and said piercing and interengaging means includes a plurality of substantially helical needles mounted on said base and extending substantially identically from said flat surface.

4. A device as in claim 3 in which said disc is symmetrical about a central axis normal to said surface and said needles are disposed symmetrically about said axis.

5. A device as in claim 3 including a straight needle on said base and projecting therefrom along said axis.

6. A device as in claim 3 including a plate engaged by all of said needles.

7. A device as in claim 1 including a bar on said base, said bar having a reentrant edge groove therein, and a pawl sheet adapted to engage a catheter in said groove and to slide on said catheter into a position abutting said bar for inhibiting longitudinal movement of said catheter in one direction in said groove.

* * * * *